(12) United States Patent
Wallace

(10) Patent No.: US 6,476,037 B1
(45) Date of Patent: Nov. 5, 2002

(54) L-ARGININE AND PHOSPHODIESTERASE (PDE) INHIBITOR SYNERGISM

(75) Inventor: Arthur W. Wallace, San Rafael, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/644,982

(22) Filed: Mar. 23, 2000

(51) Int. Cl.$^7$ .............................................. A01N 43/54
(52) U.S. Cl. ....................... 514/258; 514/262; 514/253; 514/565
(58) Field of Search ............................... 514/505, 262, 514/253, 258

(56) References Cited

U.S. PATENT DOCUMENTS

| | | | | |
|---|---|---|---|---|
| 5,767,160 A | * | 6/1998 | Kaesemeyer | 514/565 |
| 5,891,459 A | * | 4/1999 | Cooke et al. | 424/439 |
| 5,919,474 A | | 7/1999 | Place et al. | |
| 5,958,926 A | * | 9/1999 | Garvey et al. | 514/253 |
| 6,071,272 A | * | 6/2000 | Hoffman et al. | 604/500 |
| 6,127,363 A | | 10/2000 | Doherty, Jr. et al. | |
| 6,156,753 A | | 12/2000 | Doherty, Jr. et al. | |
| 6,207,713 B1 | * | 3/2001 | Fossel | 514/565 |
| 6,277,884 B1 | * | 8/2001 | de Tejada | 515/565 |
| 6,284,763 B1 | * | 9/2001 | Adams et al. | 514/211.07 |
| 6,300,335 B1 | | 10/2001 | Campbell et al. | |
| 2002/0035067 A1 | * | 3/2002 | Adams et al. | 514/18 |

FOREIGN PATENT DOCUMENTS

| | | |
|---|---|---|
| WO | WO 98/19672 | 5/1998 |
| WO | WO 98/58633 | 12/1998 |
| WO | WO 99/51252 | 10/1999 |
| WO | WO 00/00212 | 1/2000 |
| WO | WO 00/15233 | 3/2000 |

OTHER PUBLICATIONS

PCT Search Report for International Application No. PCT/US01/08863.

Wallace and Tom (2000) "Interaction of L–Arginine and Phosphodiesterase inhibitors in Vasodilation of the Porcine Internal Mammary Artery", Anesth. Analg. 90: 840–846.

Ballard (1998) "Effects of Sildenafil on the relaxation of human corpus cavernosum tissue in vitro and on the activities of cyclic nucleotide phsophodiesterase isozymes" J. Urology, 159(6) 2164–71.

Bellamy et al. (1998) "Syndrome X and endothelial dysfunction" Cardiovasc. Res., 40(2):410–417.

Bossaller (1987) "Impaired cholinergic vasodilation in the cholesterol–fed rabbit in vivo" Basic Res. Cardiol., 82(4):396–404.

Ceremuzynski et al. (1997) "Effect of Supplemental Oral L–Arginine on Exercise Capacity in Patients With Stable Angina Pectoris." Am. J. Cardiol., 80(3):331–333.

Chester et al. (1990) "Low basal and stimulated release of nitric oxide in atherosclerotic epicardial coronary arteries." Lancet, 336(8720):897–900.

Clarkson et al. (1996) "Oral L–Arginine Improves Endothelium–dependent Dilation in Hypercholsterolemic Young Adults." J. Clin. Invest., 97:1989–1994.

Creager et al. (1992) "L–Arginine Improves Endothelium–dependent Vasodilation in Hypercholesterolemic Humans." J. Clin. Invest., 90:1248–1253.

Doherty (1997) "Oral, Transdermal, and Transurethral Therapies for Erectile Dysfunction." Male Infertility and Dysfunction, ch. 33., Hellstrom, ed., Springer Verlag, New York, N.Y.

Drexler et al. (1991) "Correction of endothelial dysfunction in coronary microcirculation of hypercholsterolaemic patients by L–arginine." Lancet, 338:1546–1550.

Egashira et al. (1996) "Effects of L–arginine Supplementation on Endothelium–Dependent Coronary Vasodilation in Patients With Angina Pectoris and Normal Coronary Ateriograms." Circulation, 94(2):130–134.

Furchgott et al. (1987) "Evidence for Endothelium–Dependent Vasodilation of Resistance Vessels by Acetylcholine." Blood Vessels, 24(3):145–149.

Golino et al. (1991) "Divergent Effects of Serotonin on CoronaryArtery Dimensions and Blood Flow in Patients with Coronary Atherosclerosis and Control Patients." N. Engl. J. Med., 324(10):641–648.

Hasdai (1997) "Coronary Endothelial Dysfunction in Humans Is Associated With Myocardial Perfusion Defects." Circulation, 96(10):3390–3395.

Hiramatsu et al (1995) "Effect of L–Arginine Cardioplegia on Recovery of Neonatal Lamb Hearts After 2 Hours of Cold Ischemia." Ann. Thorac. Surg., 60(5): 1187–1192.

Jackson et al. (1999) "Effects of Sildenafil Citrate on Human Hemodynamics." Am. J. Cardiol., 83(5A):13C–20C.

Klein et al. (1995) "Comparative study on the effects of intracoronary nicorandil and nitroglycerin in ischaemic, reperfused porcine hearts." Eur. Heart. J., 16(5):603–609.

Kobayashi et al. (1999) "Effects of Infusion of L–arginine exercise–induced myocardial ischemic ST–segment changes and capacity to exercise of patients with stable angina pectoris." Coron. Artery Dis., 10(5):321–326.

(List continued on next page.)

Primary Examiner—James H Reamer
(74) Attorney, Agent, or Firm—Tom Hunter; Quine Intellectual Property Law Group, P.C.

(57) ABSTRACT

This invention pertains to the discovery that L-arginine and type V phosphodiesterases act synergistically to inhibit vasospasm and/or to induce vasodilation. Methods are provided using combinations of L-arginine and type V phosphodiesterase inhibitors in the treatment of cardiac pathologies and/or the treatment of erectile dysfunction.

44 Claims, 3 Drawing Sheets

OTHER PUBLICATIONS

Koifman et al. (1995) "Improvement of Cardiac Performance by Intravenous Infusion of L–Arginine in Patients With Moderate Congestive Heart Failure." *J. Am. Coll. Cardiol.* 26(5):1251–1256.

Moncada et al. (1989) "The biological significance of nitric oxide formation from L–arginine." *Biochem. Soc. Trans.,* 17:642–644.

Moncada et al. (1989) "Biosynthesis of Nitric Acid from L–Argenine: A Pathway for the regulation of cell function and communication." *Biochem. Pharmacol.,* 38:1709–1715.

Nakanishi et al. (1992) "Intracoronary L–argenine during reperfusion improves endothelial function and reduces infarct size." *Am. J. Physiol.,* 263(6 Pt. 2):H1650–1658.

Palmer et al. (1988) "L–arginine is the physiological precursor for the formation of nitric oxide in endothelium–dependent relaxation." *Biochem. Biophys. Res. Commun.,* 153:1251–1256.

Pearson (1991) "Production of Endothelium–Derived Contracting Factor is Enhanced After coronary Reperfusion." *Ann. Thorac. Surg.,* 51(5):788–793.

Polson (1996) "Cyclic Nucleotide Phosphodiesterases and Vascular Smooth Muscle." *Annual Review Pharmacol.,* 26 (Suppl. 4):S13–20.

Richard et al. (1990) "Different activiation of L–arginine pathway by bradykinin, serotonin, and clonidine in coronary arteries." *Am. J. Physiol.* 1990; 259:H1433–439.

Simonetti et al. (1989) "Biphasic effect of nitrogylcerin on coronary hemodynamics in normal subjects." *Z. Kardiol.,* 78(Suppl. 2):52–55; discussion 64–7.

Ueno et al. (1995) "Effects of the New Nitrate Ester ITF 296 on Coronary and Systemic Hemodynamics in the Conscious Dog: Comparison with Nitroglycerin and Nicorandil." *J. Cardiovasc. Pharmacol.,* 26(Suppl. 4):S13–20.

Vallance et al. (1989) "Nitric oxide synthesised from L–arginine mediates endothelium dependent dilation in human veins in vivo." *Cardiovasc. Res.,* 23:1053–1057.

Vallance et al. (1989) "Effects of endothelium–derived nitric oxide on peripheral arteriolar tone in man." *Lancet,* 2:997–1000.

Vallance et al. (1989) "The interplay between platelet and vessel–wall mediators in coronary artery occlusion." *Biomed. Pharmacother.,* 43:113–119.

Wallace et al. (1999) "L–Arginine Infusion Dilates Coronary Vasculature in Patients Undergoing Coronary Bypass Surgery." *Anesthesiology,* 90:1577–1586.

Webb et al. (1999) "Sildenafil Citrate and Blood–Pressure–Lowering Drugs: Results of Drug Interaction Studies with an Organic Nitrate and a Calcium Antagonist." *Am. J. Cardiol.,* 83(5A):21C–28C.

Yoneyama et al. (1990) Nicorandil Increases Coronary Blood Flow Predominately by K–Channel Opening Mechanism. Cardiovasc. Drugs Ther., 4(4):1119–1126.

* cited by examiner

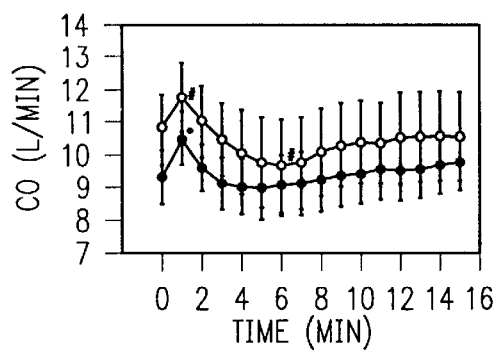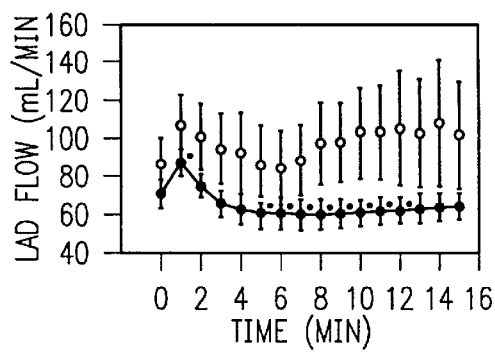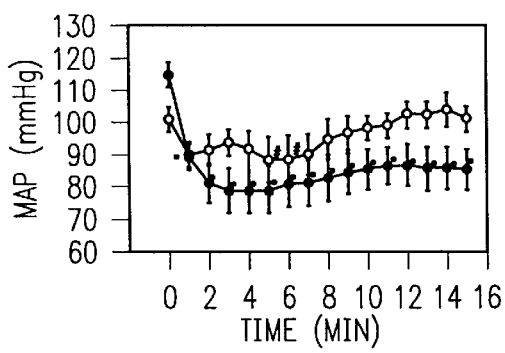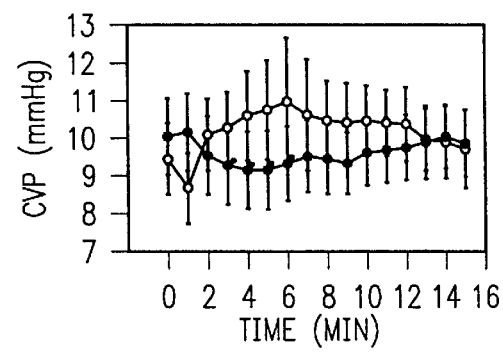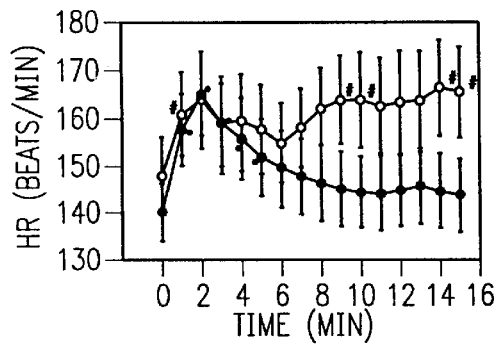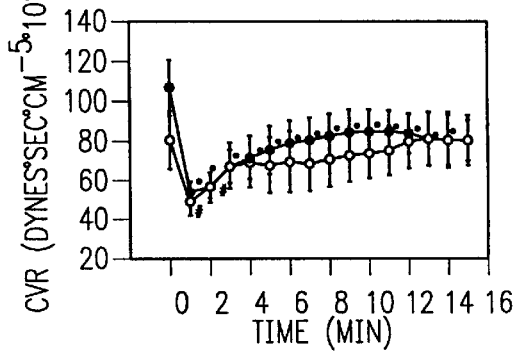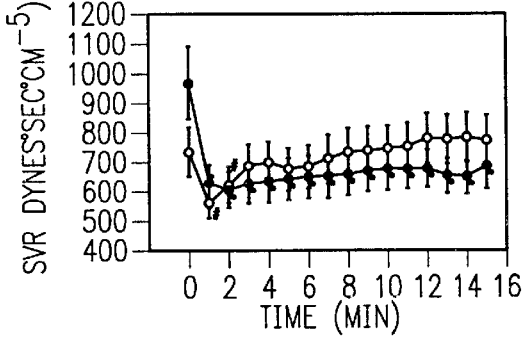

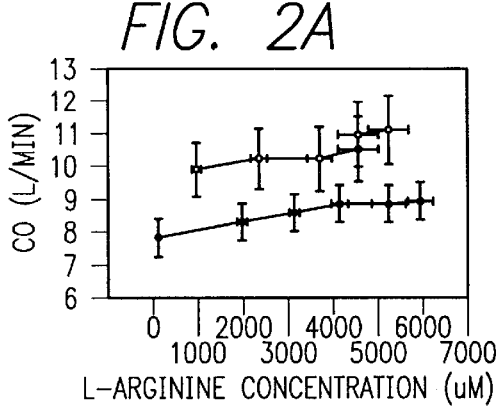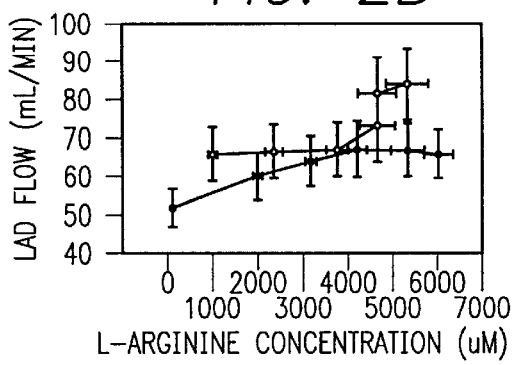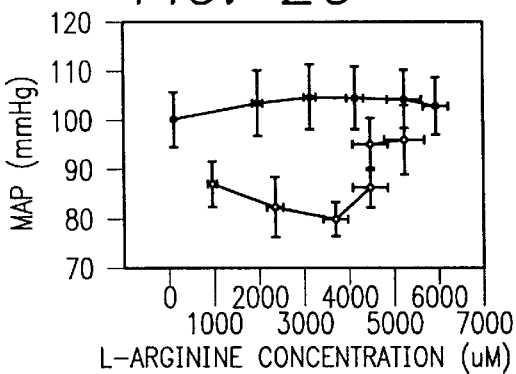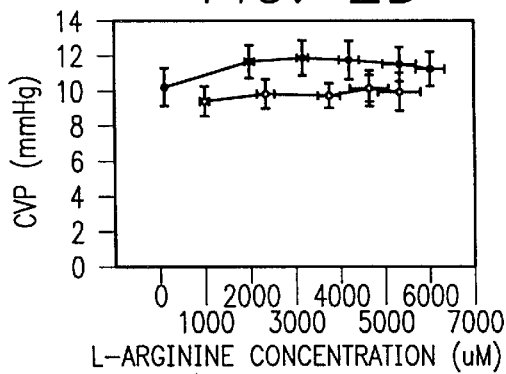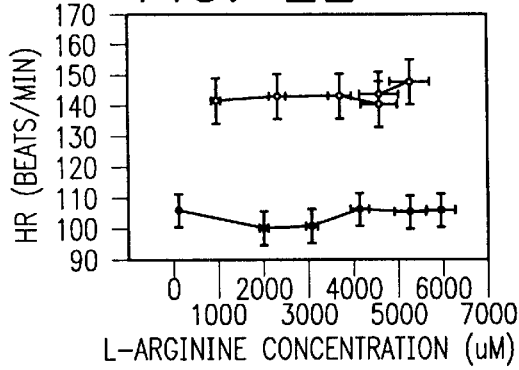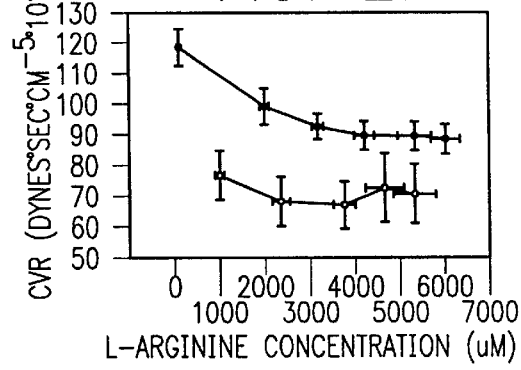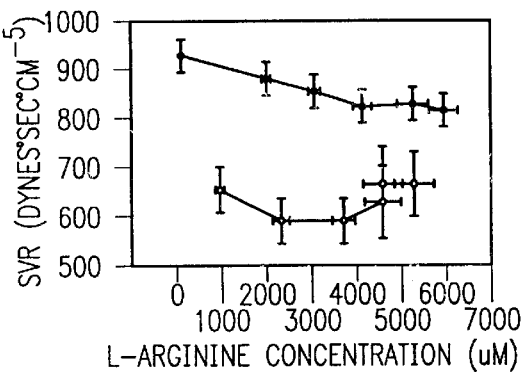
FIG. 2G

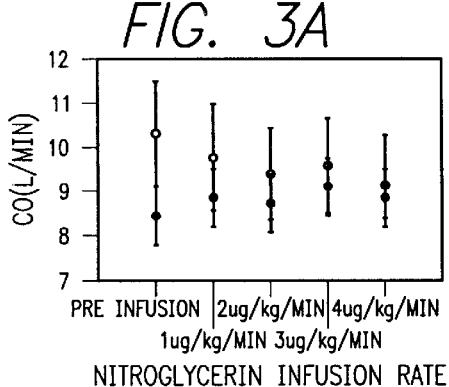
FIG. 3A
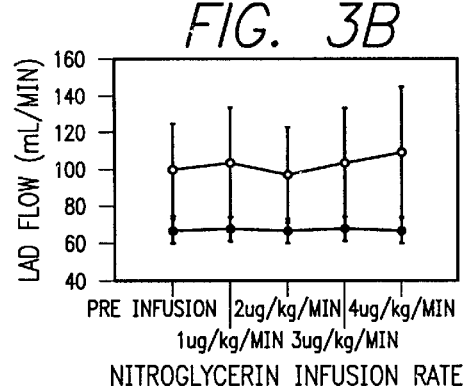
FIG. 3B
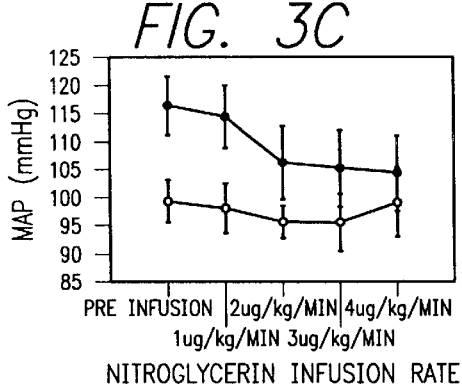
FIG. 3C
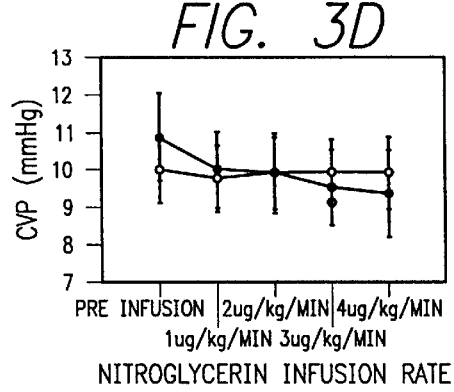
FIG. 3D
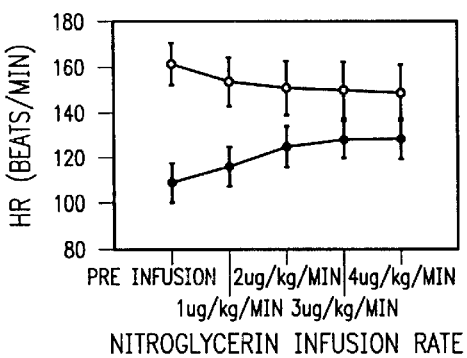
FIG. 3E
FIG. 3F
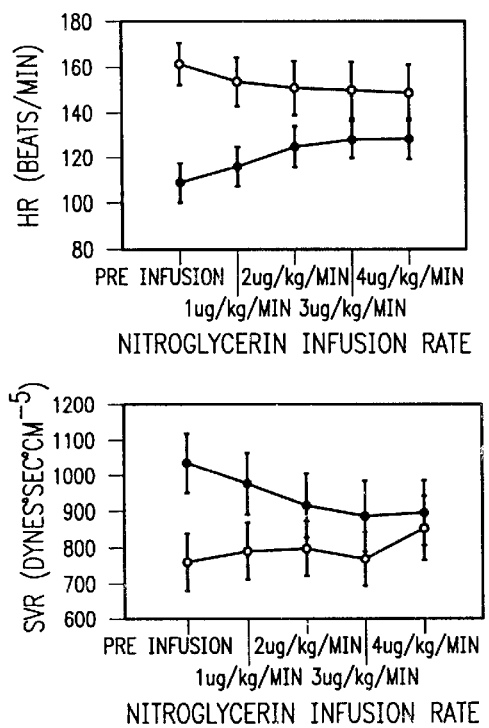
FIG. 3G

L-ARGININE AND PHOSPHODIESTERASE (PDE) INHIBITOR SYNERGISM

STATEMENT AS TO RIGHTS TO INVENTIONS MADE UNDER FEDERALLY SPONSORED RESEARCH AND DEVELOPMENT

This invention was made with Government support by the Veteran's Administration. The Government of the United States of America may have certain rights in this invention.

CROSS-REFERENCE TO RELATED APPLICATIONS

[Not Applicable]

FIELD OF THE INVENTION

This invention relates the regulation of vascular hemodynamics in various pathologies. In particular this invention pertains to the discovery that L-arginine and type V phosphodiesterases act synergistically to inhibit vasospasm and/or to induce vasodilation.

BACKGROUND OF THE INVENTION

Impotence (erectile dysfunction) is the consistent inability to achieve or sustain an erection of sufficient rigidity for sexual intercourse. It has recently been estimated that approximately 10 million American men are impotent (Shabsigh et al. (1988) *Urology*32: 83–90; Furlow (1985) *Med Aspects Hum. Sex.* 19:13–16). Impotence is recognized to be an age-dependent disorder, with an incidence of 1.9 percent at 40 years of age and 25 percent at 65 years of age (Kinsey et al. (1948) pages 218–262 in *Sexual Behavior in the Human Male*; A. C. Kinsey et al., eds., Philadelphia, Pa.: W. B. Saunders). In 1985 in the United States, impotence accounted for more than several hundred thousand outpatient visits to physicians Rational Center for Health Statistics (National Hospital Discharge Survey, 1985, Bethesda, Md., Department of Health and Human Services, 1989 D-ES publication no. 87-1751). Depending on the nature and cause of the problem, treatments include psychosexual therapy, hormonal therapy, administration of vasodilators such as nitroglycerin and α-adrenergic blocking agents ("α-blockers-"), oral administration of other pharmaceutical agents, vascular surgery, implanted penile prostheses, vacuum constriction devices and external aids such as penile splints to support the penis or penile constricting rings to alter the flow of blood through the penis.

Recent approaches to the treatment of impotence involve the use of type V phosphodiesterase inhibitors (e.g. Viagra™) increase vasodilation. Viagra™, has demonstrated significant side effects. In addition, interaction with other systemically administered medications has posed substantial risks.

Vasodilators been of interest and some use in the management of heart disease, in particular in the management of perioperative myocardial ischemia and, in certain cases, in the management of acute myocardial infarction. One of the possible etiologies of perioperative myocardial ischemia is impaired endothelium-dependent coronary flow (Hasdai (1997) *Circulation*, 96(10): 3390–3395). Endothelial cells contribute to the control of local vascular tone by formation of nitric oxide (NO) (Furchgott et al. (1987) *Blood Vessels*, 24(3): 145–149). In patients with atherosclerotic coronary arteries, basal secretion of NO is lower (Chester et al. (1990) *Lancet*, 336(8720): 897–900) and NO-mediated endothelium-dependent relaxations fail to occur. (Chester et al. supra.; Bossaller (1987) *Basic Res Cardiol*, 82(4): 396–404; Golino et al. (1991) *N Engl J Med.*, 324(10): 641–648). As a consequence, NO-dependent factors which cause vasodilation in normal coronary arteries, paradoxically cause vasoconstriction in atherosclerotic vessels (Golino et al. supra.). Endothelial dysfunction may result in platelet adhesion, aggregation, and platelet-induced contractions of coronary smooth muscle, and thus facilitate events such a vasospasm, myocardial ischemia, and coronary thrombosis (Pearson (1991) *Ann Thorac Surg*, 51(5): 788–793).

SUMMARY OF THE INVENTION

In particular this invention pertains to the discovery that L-arginine and type V phosphodiesterases act synergistically to inhibit vasospasm and/or to induce vasodilation. The combination is particularly useful in the treatment of erectile dysfunction and/or various cardiac pathologies. Thus, in one embodiment, this invention provides methods for ameliorating erectile dysfunction in a male individual. The methods involve administering to the individual an effective amount of a pharmaceutical composition comprising a type V phosphodiesterase inhibitor and L-arginine. In preferred embodiments, the type V phosphodiesterase inhibitor zaprinast; dipyridamole; pyrazolopyrimidinones; griseolic acid derivatives; 2-phenylpurinones; phenylpyridone derivatives; pyrimidines; pyrimidopyrimidines; purines; quinazolines; phenylpyrimidinones; imidazoquinoxalinones or aza analogues thereof; phenylpyridones; 4-bromo-5-(pyridylmethylamino)-6-[3-(4-chlorophenyl)propoxy]-3 (2H)pyridazinone; 1-[4-[(1,3-benzodioxol-5-ylmethyl) amiono]-6-chloro-2-quinazolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5] imidazo[2,1-b]purin-4(3H)one; furazlocillin; cis-2-hexyl-5-methyl-3,4,5,6a,7,8,9,9a-octahydrocyclopent[4,5]imidazo [2,1- b]purin-4-one; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; and 1-[4[(1,3-benzodioxol-5-ylmethyl) amino]-6-chloro-2-quinazolinyl]4-piperidinecarboxylic acid, or combinations thereof. In particularly preferred embodiments, the phosphodiesterase inhibitor is zaprinast, or a pyrazolopyrimidinone, or sildenafil. The method may further involve administering to the individual a beta blocker to prevent an excessive heart rate leading to ischemia. In one embodiment, the individual is given a daily dose of phosphodiesterase inhibitor in the range of approximately 0.1 to 500 mg/day. The phosphodiesterase inhibitor is can be formulated as a unit dosage pharmaceutical formulation. In certain embodiments, this method is used to amelioriate vasculogenic impotence.

In another embodiment, this invention provides methods of inducing vasodilation or inhibiting vasospasm of a coronary artery or bypass graft. The methods involve contacting the coronary artery or bypass graft with L-arginine and a type V phosphodiesterase inhibitor, whereby L-arginine and the type V phosphodiesterase inhibitor act synergistically to induce or increase vasodilation or to inhibit vasospasm of the coronary artery or bypass graft. In one embodiment, the L-arginine is preferably administered at a concentration ranging from about $10^{-5}$ M to about $10^{-2}$ M and the type V phosphodiestersase inhibitor is administered at a concentration sufficient to inhibit vasospasm (in combination with the L-arginine). In certain embodiments, the phosphodiesterase inhibitor concentration ranges from about $1 \times 10^{-7}$ M to about $5 \times 10^{-4}$ M to inhibit vasospasm. In particularly preferred embodiments, the type V phosphodiesterase inhibitor is sildenafil administered at a concentration ranging from about $2 \times 10^{-7}$ M to about $2 \times 10^{-4}$ M, or zaprinast administered at a concentration ranging from about $5 \times 10^{-7}$ M to about $5 \times 10^{-4}$ M.

In another embodiment, the L-arginine is administered at a concentration ranging from about $10^{-5}$ M to about $10^{-2}$ M and the type V phosphodiestersase inhibitor is administered at a concentration ranging from about $10^{-7}$ M to about $10^{-4}$ M to induce vasodilation.

In certain embodiments, the L-arginine and the phosphodiestersase inhibitor are combined in a single formulation, and, optionally, combined with a pharmaceutically acceptable excipient. In particularly preferred embodiments, the L-arginine is formulated as L-arginine hydrochloride. Preferred type V phosphodiestersase inhibitors include zaprinast, sildenafilm, DMPPO, and 1-arylnaphthalene lignan series, in which 1-(3-bromo-4,5-dimethoxyphenyl)-5-chloro-3-[4-(2-hydroxyethyl)-1-piperazinylcarbonyl]-2-(methoxycarbonyl)naphthalene hydrochloride. The contacting can involve an intravenous injection of the L-arginine and/or the phosphodiesterase inhibitor or an oral administration of the L-arginine and/or the phosphodiesterase inhibitor.

In still another embodiment, this invention provides a pharmaceutical composition for inducing vasodilation or inhibiting vasospasm of a coronary artery or bypass graft. The composition comprises L-arginine and a type V phosphodiesterase inhibitor and, optionally, further comprises a pharmaceutically acceptable excipient. One or more type V phosphodiesterase inhibitors may be included and preferred phosphodiesterase inhibitors include, but are not limited to the type V phosphodiesterase inhibitors described herein, with particularly preferred phosphodiesterase inhibitors including sildenafil, and zaprinast. The composition may be formulated in a unit dosage form for inhibiting vasospasm of a coronary artery or bypass graft, and/or for inducing vasodilation and/or for amelioriating erectile dysfunction. In particularly preferred unit dosage formulations, L-arginine is delivered at a concentration ranging from about $10^{-5}$ M to about $10^{-2}$ M. Phosphodiesterase inhibitors are formulated to deliver dosages as described herein.

In still another embodiment, this invention contemplates the active ingredients after administration to an organism and thus provides, in a mammal, a coronary artery or bypass graft contacted with an exogenously supplied L-arginine and an exogenously supplied phosphodiesterase inhibitor whereby the L-arginine and the phosphodiesterase inhibitor act synergistically to induce vasodilation or reducing vasospasm of said coronary artery or bypass graft. The mammal can be a non-human test animal or a human subject. The phosphodiesterase inhibitor and/or the L-arginine are preferably present at concentrations as described herein.

This invention also provides kits for inducing vasodilation or inhibiting vasospasm of a coronary artery or bypass graft, or for amelioriating erectile dysfunction. The kits preferably comprise one or more containers containing L-arginine; and a type V phosphodiesterase inhibitor. The kits may further comprise a pharmaceutically acceptable excipient. Preferred type V phosphodiesterase inhibitors and dosages are as described herein. The kit may optionally include instructional materials teaching the synergistic combination of L-arginine and a type V phosphodiesterase inhibitor to induce vasodilation of a coronary artery or bypass graft and/or to inhibit vasospasm of a coronary artery or bypass graft and/or to amelioriate erectile dysfunction. The kit may, optionally, further comprise one or more a beta blockers.

DEFINITIONS

A "type V phosphodiesterase inhibitor" refers to an agent that reduces (e.g. selectively reduces) or eliminates the activity of a type V phosphodiesterase. In the context of the methods and compositions of this invention type V phosphodiesterase inhibitors include salts, esters, amides, prodrugs and other derivatives of the active agents (the PDE).

The term "erectile dysfunction" is intended to include any and all types of erectile dysfunction, including: vasculogenic, neurogenic, endocrinologic and psychogenic impotence ("impotence" is used here in its broadest sense to indicate an inability a periodic or consistent inability to achieve or sustain an erection of sufficient rigidity for sexual intercourse; see U.S. Pat. No. 5,242,391); Peyronie's syndrome; priapism; premature ejaculation; and any other condition, disease or disorder, regardless of cause or origin, which interferes with at least one of the three phases of human sexual response, i.e., desire, excitement and orgasm (see Kaplan (1979) *Disorders of Sexual Desire* N.Y., Brunner Mazel Book Inc.).

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. The present method of "treating" erectile dysfunction, as the term is used herein, thus encompasses both prevention of the disorder in a predisposed individual and treatment of the disorder in a clinically symptomatic individual.

The terms "beta blocker" and "beta-adrenergic receptor antagonist" are uses synonymously to refer to compounds that block, at least partially, an effect of the endogenous β-adrenergic receptor agonists (e.g., epinephrine and norepinephrine). Many β-adrenergic antagonists can also bind to and have a regulatory effect on alpha (α)-adrenergic receptors. Therefore, as used herein, β-adrenergic receptor antagonists include adrenergic receptor antagonists that can bind to α-, as well as β-adrenergic receptors.

The terms "active agent," "drug" and "pharmacologically active agent" are used interchangeably herein to refer to a chemical material or compound that induces a desired effect. In the preferred embodiment herein, the terms refer to a type V phosphodiesterase inhibitor, L-arginine, and, optionally, a beta blocker. Included are derivatives and analogs of those compounds or classes of compounds specifically mentioned which also induce the desired effect.

The term "transdermal" delivery, applicants intend to include both transdermal (or "percutaneous") and transmucosal administration, i.e., delivery by passage of a drug through the skin or mucosal tissue and into the bloodstream.

The term "body surface" will sometimes be used herein to refer to either the skin or the mucosal tissue. "Transdermal" delivery is also intended to encompass delivery of a drug by passage across scrotal tissue.

The term "topical administration" is used in its conventional sense to mean delivery of a topical drug or pharmacologically active agent to the skin or mucosa. "Carriers" or "vehicles" as used herein refer to carrier materials suitable for local drug administration. Carriers and vehicles useful herein include any such materials known in the art which is nontoxic and does not interact with other components of the composition in a deleterious manner.

By an "effective" amount of a drug or pharmacologically active agent is meant a nontoxic but sufficient amount of the drug or agent to provide the desired effect, i.e., treatment of erectile dysfunction, inhibition of vasospasm, etc.

BRIEF DESCRIPTION OF THE DRAWINGS

FIG. 1A through FIG. 1G illustrates the hemodynamic effects of sildenafil over time. The first dose of sildenafil (●) is compared to the second dose (○). Data are expressed as mean±SE. *P<0.05 compared to baseline for first dose, #P<0.05 compared to baseline for second dose. Figure 1A: Cardiac Output (CO), Figure 1B: Left Anterior Descending (LAD) Artery Blood Flow, Figure 1C: Mean Arterial Pressure (MAP), Figure 1D: Central Venous Pressure (CVP), Figure 1E: Heart Rate (HR), Figure 1F: Coronary Vascular Resistance (CVR), and FIG. 1G: Systemic Vascular Resistance (SVR).

FIG. 2A through FIG. 2G show concentration response curves of L-arginine. The hemodynamic effects of 1-arginine alone (●) and with sildenafil (○) compared. Data are expressed as mean±SE. *P<0.05 compared to baseline for 1-arginine alone, #P<0.05 compared to baseline for 1-arginine with sildenafil. FIG. 2A: Cardiac Output (CO), FIG. 2B: Left Anterior Descending (LAD) Artery Blood Flow, FIG. 2C: Mean Arterial Pressure (MAP), FIG. 2D: Central Venous Pressure (CVP), FIG. 2E: Heart Rate (HR), FIG. 2F: Coronary Vascular Resistance (CVR), FIG. 2G: Systemic Vascular Resistance (SVR).

FIG. 3A through FIG. 3G illustrate the hemodynamic effects of nitroglycerin infusion. The hemodynamic effects of nitroglycerin alone (●) and with sildenafil (○) compared. Data are expressed as mean±SE. *P<0.05 compared to baseline for nitroglycerin alone, #P<0.05 compared to baseline for nitroglycerin with sildenafil. FIG. 3A: Cardiac Output (CO), FIG. 3BA: Left Anterior Descending (LAD) Artery Blood Flow, FIG. 3C: Mean Arterial Pressure (MAP), FIG. 3D: Central Venous Pressure (CVP), FIG. 3E: Heart Rate (HR), and FIG. 3F: Coronary Vascular Resistance (CVR), FIG. 3G: Systemic Vascular Resistance (SVR)

DETAILED DESCRIPTION

This invention pertains to the discovery that 1-arginine acts synergistically with type V phosphodiesterase inhibitors to act as a vasodilator and/or to prevent vasospasm. Because the effect is synergistic (e.g. greater than a simple additive result) both the phosphodiestersase inhibitor and the L-arginine can be used in substantially lower dosages than would have been expected and reduces the likelihood of adverse side-effects. The use of a type V phosphodiesterase in combination with L-arginine may allow more selective vasodilation because the production of nitric oxide from L-arginine is regulated by the local tissue. The Type V phosphodiesterase inhibitor amplifies the effects of any NO produced. The type V Phosphodiesterase inhibitor can be used to reduce the required concentration of L-arginine to produce vasodilation and improvement in vascular function.

While infusions of 1-arginine have allegedly been shown to improve vascular function, reduce vasospasm (Clarkson (1996) *J Clin Invest*, 97(8): 1989–1994; Creager et al. (1992) *J Clin Invest*, 90(4): 1248–1253; Drexler et al. (1991) *Lancet*, 338(8782–8783): 1546–1550), and act as a coronary vasodilator (Wallace et al. (1999) *Anesthesiology*, 90(6): 1577–1586) the dose of L-arginine required for such effects has been high, with levels approaching $10^{-2}$ molar (Clarkson et al. (1996) supra; Wallace et al. supra.).

It is demonstrated herein that type V phosphodiesterase inhibitors act synergistically with 1-arginine. Simple in vitro demonstrations of such synergy, however, are not sufficient to predict an in vivo effect. Synergistic dilation of the coronary arteries might or might not have resulted in an increase in coronary blood flow depending on the overall effect on systemic hemodynamics.

Further experiments, described herein, demonstrated that combinations of 1-arginine and type V phosphodiesterase inhibitors (e.g. sildenafil) would dilate the coronary arteries and increase coronary blood flow. In particular, it is demonstrated herein that PDE V inhibitors (e.g. sildenafil) act synergistically with 1-arginine in vasodilation of the coronary vasculature in vivo in the pig. When 1-arginine and PDE V inhibitors are used in combination, a reduced dose of 1-arginine results in significant coronary vasodilation and increases in coronary blood flow. The systemic hemodynamic effects of combinations of sildenafil and nitroglycerin can easily be compensated for with augmentation of vascular volume. The phosphodiesterase type V inhibitors may be useful in augmenting the effects of 1-arginine or other nitric oxide donors.

The synergist effect type V phosphodiesterase inhibitors and 1-arginine can be exploited in a number of contexts. In one particularly preferred embodiment, combinations of L-arginine and one or more type V phosphodiesterase inhibitors are administered to a subject to ameliorate erectile dysfunction. In another preferred embodiment, combinations of L-arginine and one or more type V phosphodiesterase inhibitors are administered to a subject reduce or prevent vasospasm. In still another preferred embodiment, combinations of L-arginine and one or more type V phosphodiesterase inhibitors are administered to induce vasodilation.

Depending on the application, the optimal dosages of L-arginine and type V phosphodiesterase inhibitor will vary. For example, in treating and/or ameliorating erectile dysfunction, the type V phosphodiestersase inhibitor(s) (sildenafil) is administered at a dosage ranging from about 25 to 100 mg. Minimum $2*10^{-7}$M to a maximum of $2.6*10^{-3}$M L-arginine baseline levels are about 93±31 uM. L-arginine is administered to provide an effective dosage (30 grams) to achieve levels about 2 to 100 times above baseline. Typically this involves administering the L-arginine at a dosage ranging from about $10^{-5}$ to about $10^{-1}$M, more preferably from about $10^{-4}$ to about $10^{-2}$ M, and most preferably from about 4000 $\mu$M.

To reduce or inhibit vasospasm of a coronary artery or bypass graft, the type V phosphodiesterase inhibitor(s) are administered at a dosage ranging from about $2\times10^{-7}$ M to about $2\times10^{-4}$ M, more preferably from about $10^{-4}$ M to about $10^{-3}$ M. In this context, L-arginine is administered to provide a serum concentration about $10^{-5}$ to $10^{-2}$M, more preferably about $10^{-4}$ to about $10^{-3}$ M and most preferably about 4000 $\mu$M.

To induce vasodilation, the type V phosphodiesterase inhibitor(s) are administered at a dosage ranging from about $10^{-7}$ M to about $10^{-4}$ M, more preferably from about $10^{-5}$ to about $10^{-4}$M. In this context, L-arginine is administered to provide a serum concentration about $10^{-5}$ to $10^{-2}$M, more preferably about $10^{-4}$ to about $10^{-3}$M and most preferably about 4000 $\mu$M.

Preferred dosage ranges for these indications are summarized below in Table 1.

TABLE 1

Preferred dosage ranges of PDE and L-arginine.

| Activity | PDE serum concentration (M) | L-Arg serum concentration (M) |
|---|---|---|
| Inhibit vasospasm | about $2 \times 10^{-7}$ to about $2 \times 10^{-4}$ | about $2 \times 10^{-4}$ to about $6 \times 10^{-4}$ |
| Induce vasodilation | about $10^{-7}$ M to about $10^{-4}$ | about $2 \times 10^{-3}$ to about $8 \times 10^{-3}$ |
| Amelioriate erectile dysfunction. | about $10^{-8}$ to about $10^{-2}$, preferably about $10^{-4}$ | about $2 \times 10^{-4}$ to about $8 \times 10^{-2}$ preferably about $10^{-3}$ |

With respect to the coronary disease applications, we note that L-arginine levels without supplementation are about 116±14 mmol/L and oral administration elevates the levels to about 224±26 mmol/L with improvement in vasomotor function. Oral L-arginine supplementation (2 grams TID) which did not statistically significantly change L-Arginine levels, (99±60 vs 106±33 mmol/L) improves exercise tolerance. Intravenous infusions (10 mg/kg/min) raised L-arginine levels from about 102±5 to about 8172±122 mmol/L and caused vasodilation. In our preliminary trial a bolus of L-arginine (30 grams over 15 minutes) elevated levels (81±8 to 6900±600 μmol). In preferred embodiments, there were two fundamentally different ranges of L-Arginine levels achieved. Levels that were 1.5 to 2 times baseline and levels that were 50 to 100 times baseline. The studies that obtain levels in the 1000's of mmol/L demonstrated vasodilation while the studies that obtained levels 2 times baseline demonstrated improved endothelial function.

Computer simulation of the predicted L-arginine levels from the high dose (1 mcg/kg/min) yield levels of 420 mmol/L. (T1/2=10 minutes, Volume distribution=0.36 L/kg: obtained from our preliminary clinical and animal data). Computer simulations of the low dose (0.5 mcg/kg/min) yield levels of 260 mmol/L. These doses are in the range to improve endothelial function and prevent vasospasm but will not cause significant vasodilation.

I. Type V Phosphodiesterase Inhibitors

A wide variety of type V phosphodiesterase inhibitors are suitable for use in this invention. As indicated by their name, phosphodiesterase inhibitors reduce or block the activity of phosphodiesterases. Phosphodiesterases are a class of intracellular enzymes involved in the metabolism of the second messenger nucleotides, cyclic adenosine monophosphate (cAMP), and cyclic guanosine monophosphate (cGMP) (see, e.g., Doherty, "Oral, Transdermal, and Transurethral Therapies for Erectile Dysfunction" in Male Infertility and Dysfunction, Hellstrom, ed., Chapter 34 (New York, N.Y.: Springer-VerlagHellstrom, 1997)).

The phosphodiesterases have been classified into seven major families, types I–VII, based on amino acid or DNA sequences (Polson (1996) Annual Review Pharmacol Toxicol , 36: 403–27)(Ballard (1998) J Urology 159(6) 2164–71). The members of the family vary in their tissue, cellular and subcellular distribution, as well as their links to cAMP and cGMP pathways. For example, the corpora cavernosa contains: type III phosphodiesterases, which are cAMP-specific cGMP inhibitable; type IV phosphodiesterases, the high affinity, high-specificity cAMP-specific form; and type V phosphodiesterases, one of the cGMP-specific forms. Inhibitors specific for each of these phosphodiesterase forms are known.

Numerous phosphodiesterase inhibitors have previously been described in the literature for a variety of therapeutic uses, including treatment of obstructive lung disease, allergies, hypertension, angina, congestive heart failure and depression (see, e.g., Goodman and Gilman's The Pharmacological Basis of Therapeutics Ninth Edition, Chapter 34) and a number of these inhibitors include type V phosphodiesterase inhibitors.

Examples of type V phosphodiesterase inhibitors include, but are not limited to, zaprinast®, MY5445, dipyridamole, and sildenafil®. Other type V phosphodiesterase inhibitors are disclosed in PCT Publication Nos. WO 94/28902 and WO 96/16644. The compounds described in PCT Publication No. WO 94/28902 include pyrazolopyrimidinones. Examples of these inhibitor compounds include, but are not limited to 5-(2-ethoxy-5-morpholinoacetylphenyl)-1-methyl-3-n-propyl-1,6-dihydro-7H-pyrazolo[4,3-d]pyrimidin-7-one, 5-(5-morpholinoacetyl-2-n-propoxyphenyl)-1-methyl-3-n-propyl-1,6-dihydro-7-H-pyrazolo[4,3-d]pyrimidin-7-one, 5-[2-ethoxy-5-(4-methyl-1-piperazinylsulfonyl)-phenyl]1-methyl-3-n-propyl-1,6-dihydro-7H-pyrazolo[4,3-d]pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonyl)phenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl-3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d]pyrimidin-7-one, and 5-[2-ethoxy-5-(1-methyl-2-imidazolyl)phenyl]-1-methyl-3-n-propyl-1,6-dihydro-7H-pyrazolo[4,3-d]pyrimidin-7-one.

The phosphodiesterase inhibitors described in PCT Publication No. WO 96/16644 include griseolic acid derivatives, 2-phenylpurinone derivatives, phenylpyridone derivatives, fused and condensed pyrimidines, pyrimidopyrimidine derivatives, purine compounds, quinazoline compounds, phenylpyrimidinone derivative, imidazoquinoxalinone derivatives or aza analogues thereof, phenylpyridone derivatives, and others. Specific examples of the phosphodiesterase inhibitors disclosed in WO 96/16644 include 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid4(3H)-one, 7-methylthio-4-oxo-2-(2-propoxyphenyl)-3,4-dihydro-pyrimido[4,5-d]pyrimidine, 6-hydroxy-2-(2-propoxyphenyl)pyrimidine-4-carboxamide, 1-ethyl-3-methylimidazo[1,5a]quinoxalin-4(5H)-one, 4-phenylmethylamino-6-chloro-2-(1-imidazoloyl) quinazoline, 5-ethyl-8-[3-(N-cyclohexyl-N-methylcarbamoyl)-propyloxy]-4,5-dihydro-4-oxo-pyrido[3, 2-e]-pyrrolo[1,2-a]pyrazine, 5'-methyl-3'-(phenylmethyl)-spiro[cyclopentane-1,7'(8'H)-(3'H)-imidazo[2,1b]purin]4' (5'H)-one, 1-[6-chloro-4-(3,4-methylenedioxybenzyl)-aminoquinazolin-2-yl)piperidine-4-carboxylic acid, (6R, 9S)-2-(4-trifluoromethyl-phenyl)methyl-5-methyl-3,4,5,6a, 7,8,9,9a-octahydrocyclopent[4,5]-midazo[2,1-b]-purin-4-one, 1t-butyl-3-phenylmethyl-6-(4-pyridyl)pyrazolo[3,4-d]-pyrimid-4-one, 1-cyclopentyl-3-methyl-6-(4-pyridyl)-4,5-dihydro-1H-pyrazolo[3,4-d]pyrimid -4-one, 2-butyl-1-(2-chlorobenzyl)6-ethoxy-carbonylbenzimidaole, and 2-(4-carboxypiperidino)-4-(3,4-methylenedioxy-benzyl)amino-6-nitroquinazoline, and 2-phenyl-8-ethoxycycloheptimidazole.

Still other type V phosphodiesterase inhibitors useful in conjunction with the present invention include: IC-351 (ICOS); 4-bromo-5-(pyridylmethylamino)-6-[3-(4-chlorophenyl)propoxy]-3(2H)pyridazinone; 1-[4-[(1,3-benzodioxol-5-ylmethyl)amiono]-6-chloro-2-quinazolinyl]-4-piperidine-carboxylic acid, monosodium salt; (+)-cis-5,6a, 7,9,9,9a-hexahydro-2-[4-(trifluoromethyl)-phenylmethyl-5-methyl-cyclopent-4,5]imidazo[2,1 -b]purin-4(3H)one; furazlocillin; cis-2-hexyl-5-methyl-3,4,5,6a,7,8,9,9a-octahydrocyclopent[4,5]imidazo[2,1-b]purin-4-one; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); and Sch-51866.

Other type V phosphodiesterase inhibitors include, but are not limited to DMPPO (Eddahibi (1988) *Br. J. Pharmacol.*, 125(4): 681–688), and 1-arylnaphthalene lignan series, including 1-(3-bromo-4,5-dimethoxyphenyl)-5-chloro-3-[4-(2-hydroxyethyl)-1-piperazinylcarbonyl]-2-(methoxycarbonyl)naphthalene hydrochloride (27q) (Ukita (1999) *J. Med. Chem.* 42(7): 1293–1305).

II. Beta Blockers

It has been observed that patients, particularly patients with erectile dysfunction, show a high incidence of mortality from cardiac disease. Without being bound to a particular theory, we believe this is due to two effects: The first is patients who take sildenafil with nitroglycerine may have a drop in blood pressure and become hypotensive. The methods of this invention reduce this risk because L-Arginine has less of this effect and can be safely used to augment the effects of sildenafil (or other type V phosphodiesterase inhibitors.

A second and more serious problem with type V phosphodiesterase inhibitors (e.g., sildenafil) is due to the fact that they dilate patient's coronary arteries which makes the patient feel better. The patient then exercises or engages in other potentially vigorous activities (e.g. intercourse). The patient, in effect, exercises to a heart rate associated with ischemia and has a heart attack.

Other vasodilators have this effects as well. Calcium channel blockers (diltiazem, nifedipine, verapamil) are used to treat coronary artery disease. They vasodilate the coronary arteries and reduce the incidence of ischemia, but nevertheless they are associated with an increase in the risk of death from ischemia. The patients feel better and exercise more. The drug does not limit their heart rate so they exercise into ischemia.

A simple approach to reduce or eliminate this risk factor is to administer a beta blocker in conjunction with the phosphodiesterase inhibitor and L-arginine. The beta blocker will impose heart rate control and prevent the subject from "exercising" to ischemia. The beta blocker can be administered separately before or after administration of the phosphodiesterase inhibitor and/or L-arginine, or all the active agents can be administered together. The agents can be administered in separate formulations and/or by separate modes of administration or as a single "compound" formulation.

As used herein, a "beta blocker" also known as a "beta-adrenergic receptor antagonist" is a compound that blocks, at least partially, an effect of the endogenous β-adrenergic receptor agonists (e.g., epinephrine and norepinephrine). Many β-adrenergic antagonists can also bind to and have a regulatory effect on alpha (α)-adrenergic receptors. Therefore, as used herein, β-adrenergic receptor antagonists include adrenergic receptor antagonists that can bind to α-, as well as β-adrenergic receptors.

The two β-adrenergic receptor subtypes, $\beta_1$ and $\beta_2$, are coupled by the stimulatory guanine nucleotide-binding protein ($G_s$) to the effector enzyme, adenylyl cyclase, on the cell surface membrane of myocardial cells. When an agonist binds to the $\beta_1$ or $\beta_2$ receptor, the α subunit of $G_s$ increases its binding affinity for guanosine triphosphate (GTP), which then preferentially binds GTP over guanosine diphosphate (GDP). The $\alpha G_s$-GTP complex is a powerful stimulus for the activation of adenylyl cyclase, which generates cAMP from adenosine triphosphate (ATP). Cyclic AMP typically exerts its effect in a cell by activating cAMP-dependent protein kinase A (PKA), which in turn phosphorylates various target proteins, thereby regulating the activity of the target protein. Cyclic AMP exerts positive inotropic and chronotropic activity by increasing the flux of calcium through sarcolemmal slow $Ca^{2+}$ channels and increasing $Ca^{2+}$ uptake and release by the cytoplasmic reticulum. In addition, $\beta_1$-adrenergic receptors are coupled through $G_s$ to slow $Ca^{2+}$ channel influx by cAMP-independent pathways. Activation of these pathways leads to an increase in myosin ATPase activity, resulting in increased heart pump performance.

Many adrenergic receptor antagonists are known (see, e.g., Braunwald (1997) pages 486–488, 610–613, and 853 in *Heart Disease: A Textbook Of Cardiovascular Medicine 5th ed.*), and their tolerability can easily be evaluated, e.g., as described below. Additional adrenergic receptor antagonists can be identified by a variety of methods well known in the art. For instance, to determine if a compound is a β-adrenergic receptor antagonist, competitive binding experiments with $^{125}$I-iodocyanopindolol (ICYP), a compound which binds selectively to β-adrenergic receptors, can be employed (see, protocols in Bristow et al. (1991) *Circulation*, 84: 1024–1039; and Chidiac et al. (194) *Molec. Pharmacol.*, 45, 490–499). Competitive binding experiments with an agonist can also be employed to identify antagonists. Binding to $\beta_1$ or $\beta_2$ adrenergic receptors can be differentiated in a number of ways, such as competitive binding experiments using known $\beta_1$- or $\beta_2$-specific ligands or, preferably, using recombinant cells transformed to express only $\beta_1$- or $\beta_2$-adrenergic receptors (see, e.g., Tate et al. (1991) *Eur. J. Biochem.*, 196, 357–361; Samama et al., (1994) *Molec. Pharmacol.*, 45: 390–394; Chidiac et al., (1994) *Molec. Pharmacol.*, 45, 490–499; Yoshikawa et al, (1996) *Eur. Heart J.*, 17 (Supp. B): 8–16). Compounds binding to adrenergic receptors should be confirmed to be antagonists by a functional assay, such as adenylyl cyclase activity.

Preferred β-adrenergic receptor antagonists for use in the present invention are those with no or low intrinsic sympathomimetic activity and, preferably, low inverse agonist activity. As used herein, an adrenergic receptor antagonist having low inverse agonist activity has less than about 50% inverse agonist activity, preferably less than about 40% inverse agonist activity, and even more preferably less than about 30% inverse agonist activity. An adrenergic receptor antagonist having low intrinsic sympathomimetic activity has less than about 30% intrinsic sympathomimetic activity, more preferably less than about 20% intrinsic sympathomimetic activity, and even more preferably less than about 10% intrinsic sympathomimetic activity.

Adrenergic receptor antagonists having low intrinsic sympathomimetic activity and low inverse agonist activity may be identified as described in PCT Publication WO9844349 entitled Method For Identifying Adrenergic Receptor Antagonists Having Good Tolerability. Briefly, the basal adrenergic receptor signaling activity is measured. The basal signaling activity is the level of measurable intrinsic signaling activity of unoccupied adrenergic receptors) or any defined level of receptor signaling activity, such as the level of activity which is achieved upon stimulation of a particular receptor (e.g., a $\beta_1$-adrenergic receptor) with a specific amount of a known agonist. Adrenergic receptor signaling activity can be quantitated by measuring any cellular response initiated by adrenergic receptor signal transduction. For instance, the adenylyl cyclase activity associated with the adrenergic receptor, the heart contractility support provided by the adrenergic receptor, or the level of phosphorylation of protein kinase A associated with the adrenergic receptor can be measured. Methods of measuring adenylyl cyclase activity, heart contractility support, and level of phosphorylation of protein kinase A are known in the art (see, e.g., Samama et al., (1994) *Molec. Pharmacol.*, 45: 390–394; Chidiac et al., (1994) *Molec. Pharmacol.*, 45: 490–499; etc.). An adrenergic receptor antagonist having inverse agonist activity can be identified, for example, by its ability to decrease adenylyl cyclase activity compared to basal adenylyl cyclase activity, to inhibit heart contractility support by the adrenergic receptor compared to the basal level of heart contractility support, and/or to decrease the level of phosphorylation of protein kinase A associated with the adrenergic receptor compared to the basal level of phosphorylation of protein kinase A. An adrenergic receptor antagonist having intrinsic sympathomimetic activity can be identified, for example, by its ability to increase adenylyl cyclase activity compared to basal adenylyl cyclase activity, to increase heart contractility support provided by the adrenergic receptor compared to the basal level of heart contractility support, and/or to increase the level of phosphorylation of protein kinase A associated with the adrenergic receptor compared to the basal level of phosphorylation of protein kinase A. As can be seen from the above discussion, the basal adrenergic receptor signaling activity, the inverse agonist activity and the intrinsic sympathomimetic activity can all conveniently be measured in a single assay. For instance, adenylyl cyclase activity could be measured. An adrenergic receptor antagonist useful in the present invention would produce no more than about a 50% reduction, and less than about a 30% increase, in adenylyl cyclase activity compared to basal adenylyl cyclase activity.

In certain preferred embodiments, the β-adrenergic antagonists used in the methods and/or formulations of this invention include, but are not limited to metoprolol, carvedilol, and bucindolol Effective dosage forms, modes of administration and dosage amounts of the β-adrenergic antagonist, may be determined empirically, and making such determinations is within the skill of the art. It is understood by those skilled in the art that the dosage amount will vary with the activity of the particular agent employed, the severity of the heart failure, the route of administration, the rate of excretion, the duration of the treatment, the identity of any other drugs being administered to the patient, the age and size of the patient, and like factors well known in the medical art.

Suitable modes of administration can include, but are not limited to, oral, nasal, topical, transdermal, rectal, and parenteral routes. Preferred parenteral routes include, but are not limited to, subcutaneous, intradermal, intravenous, intramuscular and intraperitoneal routes. Preferred is oral administration.

In certain embodiments, the administration of a low dose of the β-adrenergic antagonist is begun after the patient is hemodynamically and clinically stable. The amount of the β-adrenergic antagonist may be gradually increased until an effective dose is achieved. An effective daily dose of the β-adrenergic antagonist will be that amount of the agent which is the lowest dose effective to produce a therapeutic effect and which maintains the hemodynamic and clinical stability of the patient. A suggested daily dosage of metoprolol is about 100 to 200 mg/day, a suggested daily dosage of carvedilol is about 50 mg/day, and a suggested daily dosage of bucindolol is about 100 mg/day. However, the total daily dosage of these or other β-adrenergic antagonists will be determined by an attending physician within the scope of sound medical judgment. If desired, the effective daily dose may be administered as two, three, four, five, six or more sub-doses, administered separately at appropriate intervals throughout the day.

In general, the "low dose" for beginning administration of the β-adrenergic receptor will be about 5–10% of expected final effective dose. Thus, a suggested low dose of metoprolol is about 5–20 mg/day, a suggested low dose of carvedilol is about 2.5–5.0 mg/day, and a suggested low dose of bucindolol is about 5–10 mg/day.

Treatment with the combination of full effective doses of β-blocker and phosphodiesterase inhibitor and L-arginine can be continued indefinitely, if necessary.

III. Additional Pharmacologically Active Agents

Additional pharmacologically active agents may be delivered along with the primary active agents, i.e., the phosphodiesterase inhibitor(s) and L-arginine. In one embodiment, such agents include beta blockers as described above.

This invention also contemplates the inclusion of other active agents, e.g., vasoactive agents. Suitable vasoactive agents include, but are not limited to, nitrates and like compounds such as nitroglycerin, isosorbide dinitrate, erythrityl tetranitrate, amyl nitrate, sodium nitroprusside, molsidomine, linsidomine chlorhydrate ("SIN-1"), S-nitroso-N-acetyl-d,1-penicillamine ("SNAP"), S-nitroso-N-cysteine, S-nitroso-N-glutathione ("SNO-GLU") and diazenium diolates ("NONOates"); long and short acting α-blockers such as phenoxybenzamine, dibenarnine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate and isoxsuprine; chlorpromazine; haloperidol; yohimbine; Rec 15/2739; trazodone; naturally occurring prostaglandins such as $PGE_0$, $PGE_1$, $PGA_1$, $PGB_1$, $PGF_1\alpha$ 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_3\alpha$., semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptides. Prazosin, prostaglandin $E_0$, prostaglandin $E_1$ and prostaglandin $E_2$ are particularly preferred vasoactive agents to be co-administered with the active agent(s) in the formulations of this invention.

IV. Pharmaceutical Formulations and Modes of Administration

In order to carry out the methods of the invention, one or more type V phosphodiesterase inhibitors are administered in conjunction with an L-arginine to an individual prone to erectile dysfunction and/or to a cardiac disease. While this invention is described generally with reference to human subjects, veterinary applications are contemplated within the scope of this invention. The phosphodiesterase inhibitor and the L-arginine can be administered simultaneously or sequentially with either the inhibitor or the L-arginine being administered first. Both the inhibitor and the L-arginine can be administered by the same modality (and even in the same formulation) or they can be administered in different formulations and/or by different modalities.

The phosphodiesterase inhibitor(s) and/or L-arginine (and/or optional beta blocker(s) discussed below) may be administered, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of acid moieties which may be present on a phosphodiesterase inhibitor molecule are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

The type V phosphodiesterase inhibitors and L arginine (and, optionally, beta blockers) and various derivatives and/or formulations thereof as identified herein are useful for parenteral, topical, oral, or local administration, such as by aerosol or transdermally, for prophylactic and/or therapeutic treatment of coronary disease and/or erectile dysfunction. The pharmaceutical compositions can be administered in a variety of unit dosage forms depending upon the method of administration. Suitable unit dosage forms, include, but are not limited to powders, tablets, pills, capsules, lozenges, suppositories, etc.

The type V phosphodiesterase inhibitors and L arginine (and, optionally, beta blockers) and various derivatives and/or formulations thereof are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s). The excipients are preferably sterile and generally free of undesirable matter. These compositions may be sterilized by conventional, well known sterilization techniques.

The concentration of active agent(s) (type V phosphodiestersase inhibitor(s) and/or L-arginine, etc.) can vary widely, and will be selected primarily based on fluid volumes, viscosities, body weight and the like in accordance with the particular mode of administration selected and the patient's needs. Concentrations, however, will typically be selected to provide dosages in accordance with the dosage recommendations provided above. It will be appreciated that such dosages may be varied to optimize a therapeutic regimen in a particular subject or group of subjects.

In therapeutic applications, the compositions of this invention are administered to a patient suffering from a disease (e.g., a cardiac disease and/or erectile dysfunction) in an amount sufficient to cure or at least partially arrest the disease and its complications (e.g. to increase penile tumescence in the case of erectile dysfunction, and/or to inhibit vasospasm in cardiac disease, etc.). An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

In certain preferred embodiments, the phosphodiesterase inhibitors and L-arginine are administered orally (e.g. via a tablet) or as an injectable in accordance with standard methods well known to those of skill in the art. In other preferred embodiments, the phosphodiesterase inhibitors and/or L-arginine and/or, optionally, one or more beta blockers, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Particularly in the treatment of erectile dysfunction, it is contemplated that in certain embodiments the phosphodiesterase inhibitor(s) and L-arginine are administered locally via a patch (e.g. as described above) or other topical formulation. Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

The foregoing formulations and administration methods are intended to be illustrative and not limiting. It will be appreciated that, using the teaching provided herein, other suitable formulations and modes of administration can be readily devised.

V. Kits

The invention also encompasses a kit for practicing the methods of this invention. In one embodiment the kit contains materials for amelioriating one or more symptoms of cardiac disease (e.g. for inducing vasodilation or for inhibiting coronary artery or bypass graft vasospasm) in accordance with the methods described herein. In another embodiment, the kit contains materials for amelioriating erectile dysfunction.

In preferred embodiments, the kit(s) include the pharmaceutical formulation(s) to be administered, and, optionally, a device for administering the formulation (e.g., a skin patch, a syringe, etc.). The kit may, optionally comprise a container, preferably sealed, for housing the drug and device (if present) during shipping and/or storage and prior to use. The formulation may consist of the drug(s) in unit dosage form. The kit may contain multiple formulations of different dosages of the same or different agent(s).

In addition, the kits optionally include labeling and/or instructional materials providing directions (i.e., protocols) for the practice of the methods of this invention. Preferred instructional materials teach the use of type V phosphodiesterase inhibitors in combination with L-arginine to ameliorate erectile dysfunction (i.e., to increase penile tumescence), and/or to induce vasodilation (e.g. of coronary arteries), and/or to inhibit vasospasm of coronary arteries and/or bypass grafts. The instructional material may additionally, but optionally, teach the use/inclusion of a beta blocker in the therapeutic regimen.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Synergism Between Nitric Oxide Donors and Sildenafil in the Systemic and Coronary Vasculature of the Pig This experiment tested the hypothesis that 1-arginine and the type V phosphodiesterase inhibitor sildenafil would synergistically dilate the coronary vasculature. Chronically instrumented female swine (70 kg, n=10) (ascending aortic and left anterior descending (LAD) coronary artery transit time flow probes, carotid and internal jugular pressures) were administered five doses of 1-arginine in five-minute intervals. After a period of recovery, four doses of nitroglycerin (1, 2, 3, 4 µg/kg/min) were infused. Sildenafil (100 mg IV) was administered and the 1-arginine and nitroglycerin administrations repeated. Sildenafil increased cardiac output, LAD flow, and heart rate transiently and decreased mean arterial pressure (MAP), central venous pressure (CVP), coronary vascular resistance (CVR), and systemic vascular resistance (SVR). L-arginine decreased CVR, which led to an increase in LAD flow (52.3±5.3 to 66.7±6.6 mL/min, P<0.05). Nitroglycerin decreased CVR, MAP, and CVP but had no effect on LAD flow. Sildenafil acted synergistically with 1-arginine to increase LAD flow. During sildenafil and nitroglycerin administration, MAP and CVP could be kept constant with fluid administration. The PDE V inhibitor sildenafil acts synergistically with 1-arginine to vasodilate the coronary vasculature. Sildenafil and nitroglycerin act synergistically to vasodilate the systemic vasculature.

Methods

Chronic Animal Preparation

After approval by the Institutional Animal Care and Use Committee, 70 kg female domestic swine (70.5±2.6 kg) were sedated with ketamine (25 mg/kg IM). Mask induction with isoflurane was followed by intubation with an endotracheal tube (6.0 ID 45 cm long). An angiocathether (20 gauge) was placed in an ear vein for IV fluid administration. Prophylactic antibiotics (cefazolin 1 gram IV prior to incision followed by cephalexin 500 mg PO BID) were given. The animal was ventilated with 100% oxygen and isoflurane to maintain anesthesia. A left thoracotomy (T4-5) was performed under sterile conditions. Transonics® (Ithaca, N.Y.) transit time flow probes were placed on the ascending aorta (model 28A) and the proximal left anterior descending coronary artery (3 mm, model 3S). The flow probe cables were tunneled to the animal's back. The thoracotomy was closed and air evacuated with a chest tube. The animals were given ketorolac (30 mg IV) followed by buprenorphine (0.3 to 0.6 mg IM Q8 hours for 5 days) for postoperative pain. The animals were allowed to recover for a minimum of two days before experimentation.

Drugs

The following drugs were used: mannitol (250 mg/ml; Fujisawa USA, Deerfield, Ill.); 1-arginine hydrochloride (1 g/ml; SigmaUltra, Sigma Chemical Company, St. Louis, Mo.); nitroglycerin (5 mg/ml; Abbott Laboratories, North Chicago, Ill.); and sildenafil (1 mg/ml; Viagra®, Pfizer Pharmaceuticals, New York, N.Y.). L-arginine and sildenafil were dissolved and filtered in 0.9% sodium chloride solution.

Experimental Preparation

Previously instrumented swine were sedated with ketamine (25 mg/kg IM) and mask-induced with isoflurane. An angiocatheter (20 gauge) was placed in an ear vein for IV fluid administration. Animals were intubated (6.0 ID 45 cm long tube) and ventilated with 100% oxygen and isoflurane. Prophylactic antibiotics were given (cefazolin 1 gm IV). The animal's neck was then opened using sterile technique. Angiocatheters (16 gauge) were placed in the left and right internal jugular veins for central venous pressure monitoring and for drug and fluid infusions. An angiocatheter (20 gauge) was placed in the common carotid artery for blood sampling and pressure measurement. Arterial and central venous pressures were measured with disposable pressure transducers (Abbott Critical Care Systems Transpac® IV, North Chicago, Ill.) and the Transonics® Transit Time Flow meter (Model 206 with (-R) pRessure Option, Ithaca, N.Y.). ECG was monitored (Electronics for Medicine Monitor Model OM). The neck was closed. A supra-pubic bladder catheter was placed using sterile technique for urinary drainage. Data was recorded at 100 Hz using WinDaq data acquisition software (Transonics Systems, Ithaca, N.Y.). The pressure transducers were calibrated using a mercury manometer. Flow probes were calibrated prior to use.

Experimental Procedure

Fentanyl (2 mg), diazepam (20 mg), and pancuronium (10 mg) were administered as a bolus. Isoflurane was simultaneously discontinued. A continuous infusion of fentanyl (50 ug/kg/hr) and diazepam (250 ug/kg/hr) was begun. Additional pancuronium (10 mg boluses) was administered as needed. After a thirty minute period of equilibration, data recording was initiated.

1. Mannitol Administration: Baseline data was recorded for 5 minutes. A blood sample was taken prior to and 5 minutes after a bolus of mannitol (12.5 grams in 50 mL) for measurement of levels of 1-arginine, 1-citrulline, and osmolality. Ten minutes were allowed to elapse after the sampling.

2. L-Arginine Administration: A bolus dose of 1-arginine (60 cc of 10% 1-arginine (6 grams)) was administered intravenously. Five minutes later a blood sample was taken. The dose was then repeated. This procedure was repeated a total of five times (total of 300 cc of 10% 1-arginine (30 grams) administered). Thirty minutes were allowed to elapse and then a final blood sample collected.

3. Nitroglycerin Administration: A continuous intravenous infusion of nitroglycerin was begun at 1 ug/kg/min. Every ten minutes the infusion was increased by 1 ug/kg/min steps up to a final dose of 4 ug/kg/min. The infusion was then discontinued and the animal allowed to recover for 30 minutes.

4. Sildenafil Administration: Sildenafil tablets (two×100 mg) were ground with mortar and pestal, dissolved in sterile saline (200 ml), and filtered to obtain a final concentration of 1 mg/cc. A bolus dose (100 cc=100 mg) of sildenafil was administered intravenously (I.V.) and the animal allowed to equilibrate for 15 minutes.

5. Repeat of L-Arginine Administration: Five (6 gram) bolus doses of 1-arginine (total dose 30 grams) were administered (I.V.) as before followed by a 30 minute recovery period.

6. Sildenafil Administration Repeated: Preliminary trials found that a repeat dose of sildenafil was required prior to nitroglycerin administration. A 100 mg bolus of sildenafil was administered (I.V.) prior to infusion of nitroglycerin and the animal allowed to recover for 15 minutes.

7. Repeat of Nitroglycerin Administration: Four (I.V.) infusions (ten minutes each) of nitroglycerin (1, 2, 3, and 4 µg/kg/min) were given as before. During these infusions, arterial and central venous pressures were maintained constant by increasing blood volume with infusions of lactated Ringer's solution (McGaw, Inc., Irvine, Calif.).

Laboratory Analysis

Blood samples were collected in serum separator tubes and immediately placed on ice. Tubes were centrifuged for 20 minutes and the serum removed and stored in cryovials at −80° C. L-arginine and 1-citrulline levels were quantified by the Protein Structure Lab at the University of California, Davis (Davis, Calif.) with an ion-exchange chromatographer (Beckman 6300 aminoacid analyzer, Fullerton, Calif.). Serum osmolality was measured using an osmometer (Advanced Instruments, Needleham Heights, Mass.) by the Veterinary Medical Teaching Hospital Diagnostic Laboratories (Davis, Calif.).

Data Analysis

Two minute averages of mean arterial pressure (MAP), central venous pressure (CVP), cardiac output (CO), left anterior descending coronary artery flow (LAD flow), and heart rate (HR) were measured using custom software (LabView, National Instruments, Austin, Tex.). Coronary vascular (CVR) and systemic vascular resistances (SVR) were calculated using:

$$CVR = 80 \times \frac{\text{Diastolic Blood Pressure} - \text{Central Venous Pressure}}{\text{Graft Blood Flow}} \ (\text{dynes} \cdot \text{sec} \cdot \text{cm}^{-5})$$

$$SVR = 80 \times \frac{\text{Mean Arterial Pressure} - \text{Central Venous Pressure}}{\text{Cardiac Output}} \ (\text{dynes} \cdot \text{sec} \cdot \text{cm}^{-5})$$

Statistical Analysis

Repeated measures analysis of variance (ANOVA) with correction for multiple comparisons (Dunnett's test compared with baseline control group) was used to test for significance of hemodynamic changes with drug infusions (SigmaStat Version 2.03, SPSS Inc., Chicago, Ill.). Levels of 1-citrulline were compared with the Student's t-test. All results are reported as mean±standard error (SE). $P \leq 0.05$ was taken as significant for all statistical analyses (significance indicated with *, #, and † in tables and figures).

Results

The first administration of sildenafil increased cardiac output (baseline 9.3±0.8 vs. peak of 10.5±0.8 L/min, P<0.05), LAD flow (baseline 71.1±7.3 vs. peak of 87.6±7.3 mL/min, P<0.05), and heart rate (baseline 139.6±6.5 vs. peak of 165.0±8.9 beats/min, P<0.05). Mean arterial pressure (baseline 114.8±3.8 vs. min. of 78.7±7.0 mmHg, P<0.01), central venous pressure (baseline 10.0±1.0 vs. min. of 9.1±1.1 mmHg, P<0.01), coronary vascular resistance (baseline 108.2±13.9 vs. min. of 54.7±5.3 dynes*sec*cm⁻⁵*10³, P<0.01), and systemic vascular resistance (baseline 987.1±126.5 vs. min. of 612.2±61.1 dynes*sec*cm⁻⁵, P<0.01) all decreased. The duration of these effects differed (FIG. 1). The first dose of sildenafil caused a 1.2 L/min increase in cardiac output that disappeared after three minutes. Its effects on LAD flow were of similar duration. The increase in heart rate lasted about five minutes. The effects of the first dose of sildenafil on MAP, CVP, CVR, and SVR persisted through the fifteen-minute observation period before subsequent 1-arginine bolus administration. The two doses of sildenafil were similar in their effects (ANOVA, P not significant).

Serum concentrations of 1-arginine increased significantly as 1-arginine was given intravenously (P<0.01) (Table 2). Each dose was significantly higher in concentration than the previous (P<0.01). Serum levels of 1-citrulline increased with 1-arginine administration; baseline 1-citrulline was 53.2±4.1 μM and the concentration peaked five minutes after the fourth dose (61.5±6.7 μM).

TABLE 2

Serum L-Arginine and L-Citrulline Concentrations Associated with Each Dose of L-Arginine

| L-Arginine Dose (No Sildenafil) | [L-Arginine] (uM) | P-Value | [L-Citrulline] (uM) | P-Value |
|---|---|---|---|---|
| Baseline | 160.8 ± 10.9 | | 53.2 ± 4.1 | |
| Dose #1 | 1987.0 ± 116.8 | P < 0.01 | 54.7 ± 5.2 | NS |
| Dose #2 | 3139.2 ± 129.6 | P < 0.01 | 53.2 ± 4.2 | NS |
| Dose #3 | 4143.3 ± 205.4 | P < 0.01 | 54.9 ± 4.4 | NS |
| Dose #4 | 5232.7 ± 364.6 | P < 0.01 | 61.5 ± 6.7 | P < 0.05 |
| Dose #5 | 5922.1 ± 307.4 | P < 0.01 | 60.2 ± 5.9 | NS |
| 30 min Post | 2592.7 ± 268.9 | P < 0.01 | 60.5 ± 7.1 | NS |

P-values test for significant change in amino acid concentration relative to baseline levels,
NS = not significant Administration of 1-arginine increased cardiac output (P<0.01) and LAD flow (P<0.01) (Table 3). It significantly decreased coronary vascular resistance and systemic vascular resistance (P<0.01) in a dose-dependent manner (FIG. 2A, FIG. 2B, FIG. 2F, and FIG. 2G). L-arginine did not significantly affect mean arterial pressure, central venous pressure, or heart rate (FIG. 2C, FIG. 2D, and FIG. 2E). Sildenafil potentiated the effects of 1-arginine on LAD flow (P<0.05). There were greater increases in LAD flow as 1-arginine concentration was increased in the presence of sildenafil than in its absence (FIG. 2B). Sildenafil did not increase the magnitude of the effect of 1-arginine on CVR (FIG. 2F).

TABLE 3

Effects of L-Arginine Without and With Sildenafil on Hemodynamic Parameters

| | Pre | Max Effect | P-Value |
|---|---|---|---|
| L-Arginine | | | |
| CO (L/min) | 7.8 ± 0.6 | 8.9 ± 0.5 | P < 0.05 |
| LAD Flow (mL/min) | 52.3 ± 5.3 | 66.7 ± 6.6 | P < 0.05 |
| MAP (mmHg) | 100.7 ± 5.5 | 107.4 ± 6.4 | NS |
| CVP (mmHg) | 10.3 ± 0.7 | 12.0 ± 1.0 | NS |
| HR (beats/min) | 106.0 ± 5.6 | 106.5 ± 6.7 | NS |
| CVR (dynes*sec*cm⁻⁵*10³) | 119.2 ± 6.2 | 89.1 ± 4.7 | P < 0.05 |
| SVR (dynes*sec*cm⁻⁵) | 939.1 ± 36.1 | 825.0 ± 39.3 | P < 0.05 |
| L-Arginine + Sildenafil | | | |
| CO (L/min) | 9.9 ± 0.8 | 11.1 ± 1.1 | P < 0.05 |
| LAD Flow (mL/min) | 65.8 ± 6.1 | 84.7 ± 9.5 | P < 0.05 † |
| MAP (mmHg) | 87.3 ± 4.7 | 80.2 ± 3.5 | NS |
| CVP (mmHg) | 9.5 ± 0.9 | 10.2 ± 1.0 | NS |
| HR (beats/min) | 142.4 ± 9.1 | 148.7 ± 8.4 | NS |
| CVR (dynes*sec*cm⁻⁵*10³) | 77.2 ± 7.9 | 67.5 ± 7.7 | P < 0.05 |
| SVR (dynes*sec*cm⁻⁵) | 656.1 ± 50.2 | 592.1 ± 57.5 | P < 0.05 |

The P-value test significance of the peak effect compared to the baseline value before l-arginine administration ("Pre").
In the bottom table, baseline values were measured after sildenafil was given, but before l-arginine administration.
NS = not significant.
† The difference between the maximum effect and baselline value of LAD flow was significant (P < 0.05) compared to the difference between the two values when L-Arginine was given alone.

The P-value tests significance of the peak effect compared to the baseline value before 1-arginine administration ("Pre"). In the bottom table, baseline values were measured after sildenafil was given, but before 1-arginine administration. NS=not significant. † The difference between the maximum effect and baseline value of LAD flow was significant (P<5

0.05) compared to the difference between the two values when L-Arginine was given alone.

Nitroglycerin decreased MAP (P<0.01), CVP (P<0.01), CVR (P<0.05), and SVR (P<0.01) in a dose-dependent manner (FIG. 3). The response leveled off as the concentration infused reached 4 ug/kg/min. Nitroglycerin increased HR (P<0.05). It did not have a significant effect on CO or LAD flow (Table 4).

TABLE 4

Effects of Nitroglycerin Without and With Sildenafil on Hemodynamic Parameters

|  | Pre | Max Effect | P-Value |
|---|---|---|---|
| Nitroglycerin |  |  |  |
| CO (L/min) | 8.5 ± 0.6 | 9.1 ± 0.7 | NS |
| LAD Flow (mL/min) | 65.2 ± 6.6 | 65.4 ± 6.7 | NS |
| MAP (mmHg) | 115.8 ± 4.9 | 103.9 ± 6.6 | P < 0.05 |
| CVP (mmHg) | 10.8 ± 1.1 | 9.9 ± 1.0 | P < 0.05 |
| HR (beats/min) | 109.2 ± 8.7 | 128.3 ± 9.0 | P < 0.05 |
| CVR (dynes*sec*cm$^{-5}$* 10$^3$) | 109.9 ± 10.4 | 98.9 ± 9.8 | P < 0.05 |
| SVR (dynes*sec*cm$^{-5}$) | 1033.9 ± 85.0 | 882.8 ± 98.6 | P < 0.05 |
| Nitroglycerin + Sildenafil |  |  |  |
| CO (L/min) | 10.3 ± 1.2 | 9.1 ± 1.2 | NS |
| LAD Flow (mL/min) | 99.2 ± 25.7 | 108.5 ± 35.8 | NS |
| MAP (mmHg) | 99.0 ± 3.8 | 95.3 ± 4.8 | NS |
| CVP (mmHg) | 9.9 ± 0.9 | 9.7 ± 0.9 | NS |
| HR (beats/min) | 162.4 ± 8.8 | 148.8 ± 12.9 | NS |
| CVR (dynes*sec*cm$^{-5}$* (10$^3$) | 77.9 ± 12.0 | 86.7 ± 14.9 | NS |
| SVR (dynes*sec*cm$^{-5}$) | 7 60.1 ± 79.7 | 8 49.8 ± 90.7 | NS |

The P-value tests significance of the peak effect compared to the baseline value before nitroglycerin infusion ("Pre"). In the bottom table, baseline values were measured after sildenafil administration but before nitroglycerin infusion. NS=not significant As seen in FIG. 3C and FIG. 3D, MAP and CVP were maintained constant during nitroglycerin infusion following sildenafil administration by increasing fluid administration to increase blood volume (500 cc of lactated Ringer's solution). The other hemodynamic parameters did not change significantly when sildenafil and nitroglycerin were given sequentially and pressures kept constant (Table 4).

Intravenous bolus administration of mannitol (12.5 grams) resulted in an increase in serum osmolality (Δ+8.1±24.3 mosmol/kg sample) and an increase in LAD flow (Δ+5.5±0.2 mL/min) from baseline levels. Intravenous 1-arginine administration (5 doses=30 grams) also resulted in an increase in osmolality (Δ+7.7±25.0 mosmol/kg sample) and in LAD flow (Δ+14.4±0.4 mL/min) from baseline. The change in serum osmolality with mannitol administration did not differ (P not significant) from that with 1-arginine administration. The increases in LAD flow associated with mannitol and 1-arginine were significantly different from each other (P<0.01).

Discussion

L-arginine dilates the coronary vasculature in a dose-dependent fashion, resulting in an increase in flow through the left anterior descending artery (LAD). Nitroglycerin infusion does not affect LAD flow in the pig. L-arginine and the type V phosphodiesterase inhibitor sildenafil act synergistically to increase LAD flow. Nitroglycerin and sildenafil are synergistic vasodilators of the systemic vasculature but have no net effect on LAD flow. Sildenafil may be used to synergistically augment the effects of nitric oxide donors.

L-Arginine and Nitroglycerin

Augmentation of 1-arginine has been shown to improve post-ischemic recovery of cardiac mechanical function and reduce infarct size (Nakanishi et al. (192) Am J Physiol, 263(6 Pt 2): H1650–1658; Hiramatsu et al. (1995) Ann Thorac Surg, 60(5): 1187–1192). In patients with angina, 1-arginine improves endothelium-dependent vasodilation (Egashira et al. (1996) Circulation, 94(2): 130–134) and ability to exercise (Ceremuzynski et al. (1997) Am J Cardiol, 80(3): 331–333; Kobayashi et al. (1999) Coron Artery Dis., 10(5): 321–326; Bellamy et al. (1998) Cardiovasc Res, 40(2): 410–417). In patients with congestive heart failure, 1-arginine vasodilates and improves cardiac output (Koifman et al. (1995) J Am Coll Cardiol, 26(5): 1251–1256). In patients after cardiopulmonary bypass, 1-arginine is a coronary vasodilator with little effect on the systemic vasculature (Wallace (1999) Anesthesiology, 90(6): 1577–1586). The present study demonstrates a technique which may synergistically augment these effects.

Nitroglycerine and 1-arginine have distinct effects on the vasculature. This study found that nitroglycerin decreased coronary and systemic vascular resistances, which led to decreases in mean arterial and central venous pressures, but no net effect on LAD flow. There is disagreement in the literature concerning the effect of nitroglycerin on coronary blood flow, with some investigators finding an increase in flow (Ueno et al. (1995) J Cardiovasc Pharmacol, 26(Suppl 4): S13–20) and others finding no net effect (Klein et al. (1995) Eur Heart J, 16(5): 603–609). The present study found no significant change in LAD flow during intravenous infusions of nitroglycerin. While intracoronary injections of nitroglycerin increase coronary blood flow with little effect on the systemic vasculature (Klein et al. (1995) Eur Heart J, 16(5): 603–609; Yoneyama et al. (1990) Cardiovasc Drugs Ther, 4(4): 1119–1126; Simonetti et al. (1989) Z Kardiol, 78(Suppl 2): 52–55; discussion 64–7), intravenous injections decrease MAP, SVR, and CVR and result in no net change in coronary blood flow.

Effects of Sildenafil with Nitric Oxide Donors

Inhibition of type V phosphodiesterase (PDE) decreases the breakdown of cyclic GMP and promotes vascular smooth muscle relaxation. Sildenafil is the only clinically available type V PDE inhibitor and is currently used as a treatment for erectile dysfunction (Jackson et al. (1999) Am J Cardiol, 83(5A): 13C–20C). In the present study, sildenafil was found to increase cardiac output, LAD flow, mean arterial pressure, and heart rate with a peak effect at approximately two minutes following injection and to decrease coronary and systemic vascular resistances with the same profile over time. The effects of sildenafil are thus transient when administered as an i.v. bolus. Similar transient effects were also found in a clinical trial of eight healthy male subjects given sildenafil intravenously (Id.).

The interactions of sildenafil with nitric oxide donors may be of clinical use for amplification of the effects of 1-arginine (the substrate for NO production), nitroglycerin (an endothelium-independent exogenous NO donor), or other NO donors. This study tested the in vivo response to combinations of 1-arginine and sildenafil in an effort to increase the effects of 1-arginine at lower doses. The synergistic effect between 1-arginine and sildenafil on LAD flow (FIG. 2B) was likely the result of a decreased metabolism of cGMP while at the same time significantly more cyclic nucleotide was produced. Combinations of sildenafil and 1-arginine or other nitric oxide donors have the potential to be used as coronary vasodilators. It should be noted that sildenafil in combination with nitroglycerin had no effect on LAD flow, while sildenafil with 1-arginine significantly increased LAD flow.

In a small clinical trial in healthy men, sildenafil and nitroglycerin acted synergistically to decrease systolic blood pressure (Webb et al. (1999) *Am J Cardiol*, 83(5A): 21C–28C). The present study tested if blood pressure could be kept constant during the combination of nitroglycerin and sildenafil by increasing blood volume, as would be done for patients under anesthesia. Prevention of hypotension was found to be possible with minimal fluid administration (500 cc lactated Ringer's solution) (FIG. 2C and FIG. 2D). It may be possible to administer sildenafil in combination with nitric oxide donors under monitored clinical settings with synergistic improvements in coronary blood flow.

Limitations

Changes in blood osmolality affect the cardiovascular system. Hypertonic ionic (saline) and nonionic (glucose) solutions have been reported to reduce coronary vascular resistance in a direct relationship to hyperosmolality (Fleetwood et al. (1990) *Invest Radiol*, 25(3): 254–260). Could the observed changes in coronary blood flow in the present study be the result of changes in serum osmolality? Injection of mannitol resulted in a 5.5 mL/min increase in LAD flow from baseline for a change in osmolality of +8.1 mosmol/kg sample. The change in osmolality between baseline and the fifth dose of 1-arginine was +7.7 mosmol/kg sample with a change in LAD flow of +14.4 mL/min. This change in coronary blood flow was 2.6 times the change expected for a similar change in osmolality. In addition, levels of 1-citrulline, the resulting product of NO-synthase metabolism of 1-arginine, increased with 1-arginine infusion. These findings suggest that vasodilation observed during 1-arginine administration is mediated by an increase in NO synthesis, and not solely by changes in osmolality.

Why did 1-arginine drop systemic vascular resistance in pigs when it had little effect in post-bypass patients? SVR is low post-bypass and the addition of 1-arginine has minimal additional effect. In the present study, the vasculature was not dilated prior to 1-arginine infusion and could demonstrate a vasodilation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for ameliorating erectile dysfunction in a male individual, comprising administering to the individual an effective amount of a pharmaceutical composition comprising a Type V phosphodiesterase inhibitor and L-arginine.

2. The method of claim 1, wherein the Type V phosphodiesterase inhibitor is selected from the group consisting of zaprinast; dipyridamole; pyrazolopyrimidinones; griseolic acid derivatives; 2-phenylpurinones; phenylpyridone derivatives; pyrimidines; pyrimidopyrimidines; purines; quinazolines; phenylpyrimidinones; imidazoquinoxalinones or aza analogues thereof; phenylpyridones; 4-bromo-5-(pyridylmethylamino)-6-[3-(4-chlorophenyl)propoxy]-3 (2H)pyridazinone; 1-[4-[(1,3-benzodioxol-5-ylmethyl) amiono]-6-chloro-2-quinazolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5] imidazo[2,1-b]purin-4(3H)one; furazlocillin; cis-2-hexyl-5-methyl-3,4,5,6a,7,8,9,9a-octahydrocyclopent[4,5]imidazo [2,1-b]purin-4-one; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; and 1-[4[(1,3-benzodioxol-5-ylmethyl) amino]-6-chloro-2-quinazolinyl]4-piperidinecarboxylic acid, monosodium salt.

3. The method of claim 2, wherein the type V phosphodiesterase inhibitor is zaprinast.

4. The method of claim 2, wherein the Type V phosphodiesterase is a pyrazolopyrimidinone.

5. The method of claim 4, wherein the Type V phosphodiesterase is sildenafil.

6. The method of claim 1, further comprising administering to the individual a beta blocker.

7. The method of claim 1, wherein the individual is given a daily dose of phosphodiesterase inhibitor in the range of approximately 0.1 to 500 mg/day.

8. The method of claim 1, wherein the erectile dysfunction is vasculogenic impotence.

9. The method of claim 1, wherein the phosphodiesterase inhibitor is contained within a unit dosage pharmaceutical formulation.

10. A method of inducing vasodilation or inhibiting vasospasm of a coronary artery or bypass graft, said method comprising contacting the coronary artery or bypass graft with L-arginine and a type V phosphodiesterase inhibitor, whereby said L-arginine and said type V phosphodiesterase inhibitor act synergistically to induce or increase vasodilation or to inhibit vasospasm of said coronary artery or bypass graft.

11. The method of claim 10, wherein said L-arginine is administered at a concentration ranging from about $10^{-5}$ M to about $10^{-2}$ M and said type V phosphodiestersase inhibitor is administered at a concentration ranging from about $1 \times 10^{-7}$ M to about $5 \times 10^{-4}$ M to inhibit vasospasm.

12. The method of claim 11, wherein said type V phosphodiesterase inhibitor is sildenafil administered at a concentration ranging from about $2 \times 10^{-7}$ M to about $2 \times 10^{-4}$ M.

13. The method of claim 11, wherein said type V phosphodiesterase inhibitor is zaprinast administered at a concentration ranging from about $5 \times 10^{-7}$ M to about $5 \times 10^{-4}$ M.

14. The method of claim 10, wherein said L-arginine is administered at a concentration ranging from about $10^{-5}$ M to about $10^{-2}$ M and said type V phosphodiesterase inhibit is administered at a concentration ranging from about $10^{-7}$ M to about $10^{-4}$ M to induce vasodilation.

15. The method of claim 10, wherein said L-arginine and said phosphodiestersase inhibitor are combined in a single formulation.

16. The method of claim 15 wherein said L-arginine and said phosphodiestersase inhibitor are combined with a pharmaceutically acceptable excipient.

17. The method of claim 10, wherein said L-arginine is formulated as L-arginine hydrochloride.

18. The method of claim 10, wherein said phosphodiestersase inhibitor is selected from the group consisting of zaprinast, sildenafilm, DMPPO, and 1-arylnaphthalene lignan series, in which 1-(3-bromo-4,5-dimethoxyphenyl)-5-chloro-3-[4-(2-hydroxyethyl)-1-piperazinylcarbonyl]-2-(methoxycarbonyl)naphthalene hydrochloride.

19. The method of claim 10, wherein said contacting comprises an intravenous injection of the L-arginine and the phosphodiesterase inhibitor.

20. The method of claim 10, wherein said contacting comprises an oral administration of the L-arginine and the phosphodiesterase inhibitor.

21. A pharmaceutical composition for inducing vasodilation or inhibiting vasospasm of a coronary artery or bypass graft, said composition comprising L-arginine and a type V phosphodiesterase inhibitor.

22. The composition of claim 21, further comprising a pharmaceutically acceptable excipient.

23. The composition of claim 22, wherein said type V phosphodiesterase inhibitor is selected from the group consisting of sildenafil, and zaprinast.

24. The composition of claim 21, wherein said composition is in a unit dosage form for inhibiting vasospasm of a coronary artery or bypass graft, said unit dosage providing L-arginine in a concentration ranging from about $10^{-5}$ M to about $10^{-2}$ M.

25. The composition of claim 21, wherein said composition is in a unit dosage form for reducing or inhibiting vasospasm of a coronary artery or bypass graft, said unit dosage providing said phosphodiesterase inhibitor in a concentration ranging from about $2 \times 10^{-7}$ M to about $2 \times 10^{-4}$ M.

26. The composition of claim 21, wherein said composition is in a unit dosage form for inducing vasodilation of a coronary artery or bypass graft, said unit dosage providing L-arginine in a concentration ranging from about $10^{-5}$ M to about $10^{-2}$ M.

27. The composition of claim 21, wherein said composition is in a unit dosage form for inducing vasodilation of a coronary artery or bypass graft, said unit dosage providing said phosphodiesterase inhibitor in a concentration ranging from about $2 \times 10^{-7}$ M to about $2 \times 10^{-4}$ M.

28. In a mammal, a coronary artery or bypass graft contacted with an exogenously supplied L-arginine and an exogenously supplied phosphodiesterase inhibitor whereby said L-arginine and said phosphodiesterase inhibitor act synergistically to induce vasodilation or reducing vasospasm of said coronary artery or bypass graft.

29. In the mammal of claim 28, said L arginine is at a concentration ranging from about $2 \times 10^{-4}$ M to about $6 \times 10^{-4}$ M to inhibit vasospasm.

30. In the mammal of claim 28, said phosphodiesterase inhibitor is at a concentration ranging from about $2 \times 10^{-7}$ M to $2 \times 10^{-4}$ M to inhibit vasospasm.

31. In the mammal of claim 28, said L arginine is at a concentration ranging from about $2 \times 10^{-3}$ M to about $8 \times 10^{-3}$ M to induce vasodilation.

32. In the mammal of claim 28, said phosphodiesterase inhibitor is at a concentration ranging from about $10^{-7}$ M to about $10^{-4}$ M to induce vasodilation.

33. In the mammal of claim 28, said type V phosphodiesterase inhibitor is selected from the group consisting of sildenafil, and zaprinast.

34. In the mammal of claim 28, wherein said mammal is a non-human mammal.

35. A kit for inducing vasodilation or inhibiting vasospasm of a coronary artery or bypass graft, said kit comprising one or more containers containing:

L-arginine; and a type V phosphodiesterase inhibitor.

36. The kit of claim 35, further comprising a pharmaceutically acceptable excipient.

37. The kit of claim 35, wherein said type V phosphodiesterase inhibitor is selected from the group consisting of sildenafil, and zaprinast.

38. The kit of claim 35, wherein said L-arginine is in a unit dosage form for inhibiting vasospasm of a coronary artery or bypass graft, said unit dosage providing L-arginine in a concentration ranging from about $2 \times 10^{-4}$ M to about $8 \times 10^{-3}$ M.

39. The kit of claim 35, wherein said phosphodiesterase inhibitor is in a unit dosage form for reducing or inhibiting vasospasm of a coronary artery or bypass graft, said unit dosage providing said phosphodiesterase inhibitor in a concentration ranging from about $10^{-7}$ M to about $10^{-4}$ M.

40. The kit of claim 35, wherein said L-arginine is in a unit dosage form for inducing vasodilation of a coronary artery or bypass graft, said unit dosage providing L-arginine in a concentration ranging from about $2 \times 10^{-4}$ M to about $8 \times 10^{-3}$ M.

41. The kit of claim 35, wherein said phosphodiesterase inhibitor is in a unit dosage form for inducing vasodilation of a coronary artery or bypass graft, said unit dosage providing said phosphodiesterase inhibitor in a concentration ranging from about $10^{-7}$ M to about $10^{-4}$ M.

42. The kit of claim 35, further comprising instructional materials teaching the synergistic combination of L-arginine and a type V phosphodiesterase inhibitor to inhibit vasosapasm of a coronary artery or bypass graft.

43. The kit of claim 35, further comprising instructional materials teaching the synergistic combination of L-arginine and a type V phosphodiesterase inhibitor to induce vasodilation of a coronary artery or bypass graft.

44. A kit for ameliorating erectile dysfunction, said kit comprising one or more containers containing:

L-arginine;

a type V phosphodiesterase inhibitor; and a beta blocker.

* * * * *